United States Patent [19]
Berkelhammer et al.

[11] 3,991,200
[45] Nov. 9, 1976

[54] SUBSTITUTED NITROIMIDAZOLYL THIADIAZOLES AND OXADIAZOLES AS ANTIBACTERIAL AGENTS AND GROWTH PROMOTING COMPOUNDS

[75] Inventors: Gerald Berkelhammer, Princeton; Goro Asato, Titusville, both of N.J.

[73] Assignee: American Cyanamid Company, Stamford, Conn.

[22] Filed: Mar. 27, 1973

[21] Appl. No.: 562,523

Related U.S. Application Data

[60] Division of Ser. No. 463,951, April 25, 1974, Pat. No. 3,904,756, which is a division of Ser. No. 199,005, Nov. 15, 1971, Pat. No. 3,830,924, which is a continuation-in-part of Ser. No. 17,977, March 9, 1970, abandoned, which is a continuation-in-part of Ser. No. 814,205, April 7, 1969, abandoned, which is a continuation-in-part of Ser. No. 659,596, Aug. 10, 1967, Pat. No. 3,452,035, which is a continuation-in-part of Ser. No. 604,158, Dec. 23, 1966, abandoned.

[52] U.S. Cl. ................................. 424/270; 424/272
[51] Int. Cl.$^2$ ......................................... A61K 31/425
[58] Field of Search ............................ 424/270, 272

[56] References Cited
UNITED STATES PATENTS

| | | | |
|---|---|---|---|
| 3,025,303 | 3/1962 | Ifversen et al. ..................... | 424/270 |
| 3,452,035 | 6/1969 | Berkelhammer et al. ........... | 424/270 |
| 3,830,924 | 8/1974 | Berkelhammer et al. ........... | 424/270 |
| 3,842,174 | 10/1974 | Berkelhammer et al. ........... | 424/270 |

*Primary Examiner*—V. D. Turner
*Attorney, Agent, or Firm*—C. F. Costello, Jr.; J. Richards

[57] ABSTRACT

The use of substituted nitroimidazolyl-thiadiazoles and oxadiazoles are described along with methods of administration of the same. These compounds are active in enhancing the growth rate of warm-blooded animals and in controlling the growth of pathogenic microorganisms such as bacteria.

9 Claims, No Drawings

SUBSTITUTED NITROIMIDAZOLYL THIADIAZOLES AND OXADIAZOLES AS ANTIBACTERIAL AGENTS AND GROWTH PROMOTING COMPOUNDS

CROSS-REFERENCE TO RELATED APPLICATIONS

The present invention is a divisional of our Application Ser. No. 463,951, filed Apr. 25, 1974, now U.S. Pat. No. 3,904,756, which in turn is a divisional of our Application Ser. No. 199,005, filed November 15, 1971, now U.S. 3,830,924 which in turn is a continuation-in-part of our Application Ser. No. 17,977, filed March 9, 1970, now abandoned, which is a continuation-in-part of our Application Ser. No. 814,205, filed April 7, 1969, now abandoned, which is a continuation-in-part of our Application Ser. No. 659,596, filed Aug. 10, 1967, now U.S. Pat. No. 3,452,035, which in turn is a continuation-in-part of our Application Ser. No. 604,158, filed Dec. 23, 1966, now abandoned.

BACKGROUND OF THE INVENTION

The present invention describes the use and method of administration of compounds which are both highly effective at relatively low concentrations against a broad spectrum of microorganisms, and additionally provide a relatively satisfactory margin of safety. The compositions containing substituted imidazolyl compounds of the present invention are at least 5 to 10 times more active than certain distantly related imidazolyl compounds of the prior art, providing effectiveness at relatively low concentrations, as well as satisfactory margins of safety.

Imidazolyl compounds, in which the heterocyclic rings are joined by a methyleneamine bridge, have been prepared and found to have some antibacterial activity; however, such compounds have not been entirely satisfactory for these purposes. The concentration at which such compounds are active is generally much higher than the desirable level; therefore, said compounds do not provide a satisfactory margin of safety. Illustrative of said compounds which have been prepared and found to have such activity are, for example, 3-[(1-methyl-5-nitro-2-imidazolylmethylene)amino]-2-oxazolidinone and 1-[(1-methyl-5-nitro-2-imidazolylmethylene)amino]-2-imidazolidinone.

SUMMARY OF THE INVENTION

The subject matter of the present invention relates to compositions containing as the active component 1-substituted-5-nitro-2-imidazolyl compounds and an edible carrier. More particularly, the invention relates to compositions containing compounds having the following general formula:

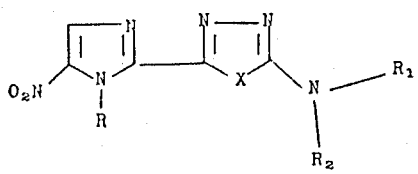

wherein R is selected from the group consisting of lower alkyl, hydroxy lower alkyl, lower alkanoyloxy lower alkyl and benzyl; X is selected from the group consisting of oxygen and sulfur; and $R_1$ and $R_2$ are selected from the group consisting of hydrogen, alkyl of 1 to 8 carbon atoms, hydroxy lower alkyl, lower alkoxy lower alkyl, cyclohexyl, formyl, lower alkanoyl, monochlorolower alkanoyl, dichlorolower alkanoyl, morpholino lower alkanoyl, lower alkyl aminolower alkyl;

taken together is selected from the group consisting of -N=CHN (lower alkyl)$_2$, piperazine, N-lower alkylpiperazine, N-hydroxy lower alkylpiperazine, N-pyridylpiperazine, N-thiazolylpiperazine, N-lower alkoxycarbonyl piperazine, piperidino and dilower alkylamino lower alkylpiperidino; and physiologically acceptable salts thereof. These salts can be, for example, the hydrochloride hydrobromide, hydroiodide, sulfate, phosphate, etc. The term "lower alkyl" as employed in the instant specification and claims is intended to include either straight or branched chain having from 1 to 4 carbon atoms. The invention relates to a method of controlling the growth of bacteria in a warm-blooded animal host which comprises administering to the animal therapeutically effective quantities of the above compounds and thereby alleviating diseases, as well as compositions of matter comprising said compounds and an edible carrier. In addition, methods are described employing the above compounds to promote the growth rate in warmblooded animals.

PREPARATION OF THE SUBSTITUTED IMIDAZOLYLS OF THE PRESENT INVENTION

In many instances the substituted imidazolyl compounds comprising the active component of the present compositions are prepared by oxidative cyclization of various thiosemicarbazones and semicarbazones of 1-substituted-5-nitro-2-imidazolecarboxaldehyde. Suitable oxidizing agents for such cyclization of the thiosemicarbazone to aminothiadiazoles include a wide variety of ferric salts such as ferric ammonium sulfate, ferric chloride, ferric nitrate, ferric acetate, sodium ferricyanide, sodium ferric oxalate, potassium ferric sulfate, and the like. The cyclizations of the semicarbazones to aminooxadiazoles are generally carried out with such agents as sodium hypobromite, sodium hypoiodite, and bromine with sodium acetate. The reactions are generally carried out at an elevated temperature between 50° and 150° C., depending on the particular moiety being prepared.

A number of the 2-(2-substituted amino-5-thiadiazolyl)-1-substituted-5-nitroimidazoles can be prepared by the reaction of 2-(2-halo-5-thiadiazolyl)-1-substituted-5-nitroimidazoles with the appropriate primary or secondary amines in an organic solvent, either in the presence of excess amine or with the use of other acid acceptors, as for example, aqueous sodium bicarbonate solution, usually at between 25° and 125° C.

In the preparation of active components having the above general formula wherein R represents a hydroxy lower alkyl group, it is often practical to first synthesize the corresponding ester, as for example, a compound of the formula:

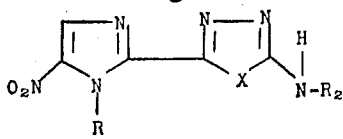

wherein R is lower alkanoyloxy lower alkyl and X and $R_2$ are as defined hereinabove, and then treat the thus formed ester with a strong mineral acid followed by pH adjustment to above about pH 7, thereby yielding the desired product. In many cases, it is found that the conditions used for cyclization 1-(2-lower alkanoyloxy lower alkyl)-5-nitro-2-imidazole carboxaldehyde thiosemicarbazones are sufficiently acidic to give rise directly to the 2-(2-amino-5-thiadiazolyl)-1-(hydroxy lower alkyl)-5-nitroimidazoles.

Where it is desired to prepare the 2-(2-formamido-5-thiadiazolyl)-1-substituted-nitroimidazole, or the 2-(2-acylamino-or 2-haloacylamino-5-thiadiazolyl)-1-substituted-5-nitroimidazole, it is practical to first synthesize the 2-(2-amino-5-thiadiazolyl)-1-substituted-5-nitroimidazole, and then treat the product with formic acid, in the case of the preparation of the 2-(2-formamido-5-thiadiazolyl)-1-substituted-5-nitroimidazole, or with an anhydride of the formula (lower alkanoyl)$_2$ or (halo lower alkanoyl)$_2$ or with the appropriate acid chloride in the instance of the preparation of the 2-(2-acylamino or 2-haloacylamino-5-thiadiazolyl)-1-substituted-5-nitroimidazole. Similar reactions can be carried out to give the corresponding oxadiazolyl compounds. These reactions are usually carried out at an elevated temperature, particularly at temperatures between 50° and 150° C.

The 2-(2-amino-5-thiadiazolyl)-1-lower alkanoyloxy lower alkyl-5-nitroimidazoles and the corresponding oxadiazolyl compounds, active components of the present compositions, can be made by esterifying the 2-(2-amino-5-thiadiazolyl or 5-oxadiazolyl)-1-hydroxy lower alkyl-5-nitroimidazoles by heating with an aliphatic acid in the presence of a mineral acid catalyst. If, instead, an aliphatic acid anhydride is employed, the products are 2-(2-lower alkanoylamino-5-thiadiazolyl or 5-oxadiazolyl)-1-lower alkanoyl lower alkyl-5-nitroimidazoles. In the latter case, a catalyst is usually not necessary. In both instances, reaction temperatures of from 50° to 150° C. are frequently employed.

For the preparation of N,N-dilower alkyl-N'-[5-(1-substituted-5-nitro-2-imidazolyl)thiadiazol-2-yl]formamidines, products of the reaction of N,N-dilower alkyl formamides with phosgene, phosphorus oxychloride, or thionyl chloride are reacted with 2-(2-amino-5-thiadiazolyl)-1-substituted-5-nitroimidazoles in an organic solvent, as for example, in an excess of the N,N-dilower alkyl formamide, usually at the ambient temperature.

The active components of the compositions of the instant invention are highly effective in controlling infections of pathogenic and other microorganisms such as *Escherichia coli, Salmonella gallinarum, Salmonella choteraesirs* Var Kunzendorf, *Proteus mirabilis, Staphylococcus aureus* strain Rose or strain Smith, *Salmonella typhosa, Klebsiella Ad, aerobacter aerogenes, Streptococcus pyogenes, Pasteurella multocida*, etc. Tests showing the use of a compound of this invention against bacteria are described in "Antimicrobial Agents and Chemotherapy-1968" page 534 etc., in a warm-blooded animal host; said active components may be administered to the warm-blooded animals, such as goats, sheep, cattle, hogs, chickens, etc., in admixture with their feed or drinking water. Furthermore, the compositions may be administered in the form of tablets, pills, capsules or the like, or parenterally by injection either intramuscularly or subcutaneously. The concentration employed in feed or water may be in the range of from 5 to 1,000 parts per million, preferably 15 to 500 parts per million; the most preferred concentration being about 50 to 200 parts per million. The above compositions have demonstrated effectiveness against Salmonella infections when the active component was administered in as little as 0.025% concentration in the diet of chicks and mice. In addition, some of the active components provide 100% control of Escherichia coli infections in chicks when administered at about 40 mg. per kg. of body weight in a single oral dose and are highly effective against a number of other bacterial infections, both gram-positive and gram-negative.

The active components of this invention can be used with pharmaceutically acceptable edible carriers in compositions such as tablets (containing 1 mg. to 100 mg. per kilogram of body weight), wherein the principal active ingredient is mixed with conventional tableting ingredients such as corn starch, lactose, sucrose, sorbitol, talc, stearic acid, magnesium stearate, dicalcium phosphate, gums, and fractionally similar materials as pharmaceutical diluents or carriers. The tablets or pills of the novel compositions can be laminated or otherwise compounded to provide a dosage form affording the advantage of prolonged or delayed action of predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach, and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The term dosage form as described herein refers to physically discrete units suitable as unitary dosage for warm-blooded animal subjects, each unit containing a predetermined quantity of active material calculated to produce the desired therapeutic effect in association with the required pharmaceutical diluent, carrier or vehicle. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The compounds of this invention have been found to promote the growth rate of warm-blooded animals, such as goats, sheep, cattle, hogs, chickens, etc. Said compounds may be administered in a manner similar to their introduction as antibacterial agents, such as orally or parenterally.

DETAILED DESCRIPTION

The following examples are provided for illustrative purposes and may include particular features of the invention; however, the examples should not be construed as limiting the invention, many variations of which are possible without departing from the spirit or scope thereof. Parts are by weight unless otherwise indicated.

EXAMPLE 1

Preparation of
2-(2-Amino-5-Thiadiazolyl)-1-methyl-5-nitroimidazole

A mixture of 4.71 gm., 0.03 mole, of 1-methyl-2-hydroxymethyl-5-nitroimidazole, and 13.3 gm., 0.03 mole, of lead tetraacetate in 200 ml. of benzene, is refluxed while stirring magnetically for about 18 hours, cooled and filtered. The filtrate is washed with 50 ml. of saturated sodium carbonate solution. The organic phase is then separated, and the aqueous phase extracted twice with 30 ml. of chloroform. The combined organic phase is then dried over magnesium sulfate. After filtering and evaporating the organic phase to dryness, the filtrate gives 4.2 gm. of pale yellow 1-methyl-5-nitro-2-imidazolecarboxaldehyde, which is dissolved in 25 ml. of hot ethanol, then added to 2.5 gm. of thiosemicarbazide in 20 ml. of boiling ethanol containing two drops of concentrated hydrochloric acid. The mixture is then boiled for a few minutes with stirring, cooled and bright yellow crystals of the thiosemicarbazone of the above aldehyde are collected. The process yields 5.3 gm., which constitutes a 77.4% overall yield, said material having a melting point of 227° C. (decomposition).

To 25 ml. of hot water containing 5.7 gm., of ferric ammonium sulfate dodecahydrate, 2.68 gm. of the above thiosemicarbazone is added, and the mixture is stirred magnetically in a boiling water bath. After 1 hour, an additional 75 ml. of hot water containing 17.1 gm. of ferric ammonium sulfate dodecahydrate is added to the above mixture. The mixture is then heated for approximately 3 hours in a boiling water bath, and filtered while still hot, yielding orange brown crystals which are washed thoroughly with hot water. The yield is 2.7 gm., having a melting point of from 259° to 260° C. (decomposition). This product is dissolved in about 20 ml. of hot dimethylformamide, filtered and the warm filtrate poured on ice. The precipitated product is washed thoroughly first with water, and then cold acetone, giving a yellow product which is dried in vacuo at 100° C. for several hours. The purified product weighs 1.55 gm., and has a melting point of from 268° to 270° C. (decomposition). The product is then submitted to analysis; calculating from carbon, hydrogen, nitrogen and sulfur, the actual values agreed closely with the theoretical values.

EXAMPLE 2

Preparation of
2-(2-Methylamino-5-thiadiazolyl)-1-methyl-5-nitroimidazole

A suspension of 20 gm. of ferric ammonium sulfate dodecahydrate in 100 ml. of water is warmed on a steam bath until the solid is completely dissolved. To the above solution 9.6 gm. 0.039 mole, of 1-methyl-5-nitro-2-imidazole-carboxaldehyde-4'-methyl-3'-thiosemicarbazone is added, and stirred on the steam bath for an additional 90 minutes. A warm solution containing 59 gm., 0.122 mole of ferric ammonium sulfate dodecahydrate in 300 ml. of water is added to the above mixture. The mixture is stirred on the steam bath for an additional 2 hours and filtered. The precipitate is washed with water and acetone to give 6.9 gm. of a yellow solid having a melting point of from 230° to 238° C. Recrystallization from 700 ml. of hot ethyl acetate gives 3.3 gm. of bright yellow needles having a melting point of 238° C.

EXAMPLE 3

Preparation of
2-(2-Dimethylamino-5-thiadiazolyl)-1-methyl-5-nitroimidazole

A mixture of 14.1 gm., 0.1 mole, of 1,2-dimethyl-5-nitroimidazole, 12 gm., 0.1 mole, of selenium dioxide and 100 ml. of diethyleneglycol dimethyl ether is refluxed while stirring magnetically for approximately 4 hours. The mixture is then cooled and filtered through a layer of diatomaceous earth into a warm solution of 11.5 gm., 0.1 mole of 4,4'-dimethyl-3'-thiosemicarbazide in 50 ml. of water and 10 ml. of glacial acetic acid. A precipitate forms immediately. The mixture is cooled and filtered to give 7.5 gm. of yellow crystals, which have a melting point of from 205° to 210° C. The crystals are recrystallized twice from methyl cellosolve and once from ethanol, to give 1.3 gm. of orange needles having a melting point of from 208° to 210° C. (decomposition).

A warm suspension of 9.2 gm. of 1-methyl-5-nitro-2-imidazolecarboxaldehyde 4',4'-dimethyl-3'-thiosemicarbazone (prepared above) in 100 ml. of water is added to a warm solution of 69.4 gm. of ferric ammonium sulfate dodecahydrate in 400 ml. of water. The mixture is magnetically stirred on a steam bath for approximately 4 hours, and filtered. The precipitate is washed with water and acetone giving 8.6 gm. of a brown solid having a melting point of from 238° to 240° C. (decomposition). Two recrystallizations from N,N-dimethylformamide gives 3.6 gm. of yellow crystals having a melting point of 252° C.

EXAMPLE 4

Preparation of
2-(2-Ethylamino-5-thiadiazolyl)-1-methyl-5-nitroimidazole and
2-(2-Dimethylamino-5-thiadiazolyl)-1-ethyl-5-nitroimidazole The ethylamino compound is prepared by employing the procedure set forth in Example 1, with the exception that ethylthiosemicarbazide is substituted for thiosemicarbazide. The compound melts at 214°-216° C.

With regard to the dimethylamino compound, said compound is prepared by employing the procedure set forth in Example 3, with the exception that 1-ethyl-2-methyl-5-nitroimidazole is utilized instead of 1,2-dimethyl-5-nitroimidazole. The process yields 1-ethyl-5-nitro-2-imidazolecarboxaldehyde, 4',4'-dimethyl-3'-thiosemicarbazone, which is cyclized as in Example 3 to 2-(2-dimethylamino-5-thiadiazoly)-1-ethyl-5-nitroimidazole.

EXAMPLE 5

Preparation of
2-(2-Formamido-5-thiadiazolyl)-1-methyl-5-nitroimidazole

The above compound is prepared by refluxing 8 gm. of 2-(2-amino-5-thiadiazolyl)-1-methyl-5- nitroimidazole in 30 ml. of 98% formic acid for 10 hours, cooling, and adding the mixture to saturated sodium bicarbonate solution, and the solid collected. The compound melts at 225° to 227° C.

EXAMPLE 6

Preparation of 2-(2-Acetamido-5-thiadiazolyl)-1-methyl-5-nitroimidazole

The above compound is prepared by heating under reflux for 30 minutes a mixture of 14 gm. of 2-(2-amino-5-thiadiazolyl-1-methyl-5-nitroimidazole in 280 ml. of acetic anhydride. The mixture is evaporated to dryness, and the solid residue is washed thoroughly with ether giving 16.4 gm. of a yellow solid having a melting point of 235° C. (decomposition).

EXAMPLE 7

Preparation of 1-(2-Acetoxyethyl)-5-nitro-2-imidazolecarboxaldehyde

A 6.27 gm. portion of 1-(2-acetoxyethyl)-2-hydroxymethyl-5-nitroimidazole is refuxed with 13.3 gm. of lead tetraacetate in 200 ml. of benzene for 18 hours, cooled, and filtered. The filtrate is washed with 50 ml. of saturated sodium carbonate solution, and the organic phase is separated therefrom. The remaining aqueous phase is twice extracted with 30 ml. of chloroform, and then combined with the above separated organic phase. The combined organic phases are dried under magnesium sulfate, and filtered. The organic solvents are then removed in vacuo, giving the above aldehyde.

EXAMPLE 8

Preparation of 2-(2-Amino-5-thiodiazolyl)-1-(2-hydroxyethyl)-5-nitroimidazole

A 14.25 g. sample of the aldehyde prepared in Example 7 is treated with 5.72 g. of thiosemicarbazide in 150 ml. of 95% ethanol containing a drop of concentrated hydrochloric acid and the mixture is heated on a steam bath for 20 minutes. The hot solution is filtered to remove insoluble materials, cooled and the yellow-brown crystals are collected. The yield of 1-(2-acetoxyethyl)-5-nitro-2-imidazolecarboxaldehyde thiosemicarbazone is 18.8 g. after drying in a vacuum oven at 60° for 2 ½ hours. Recrystallization of the product gives a yellow solid, melting point 181°–183.5° C.

The thiosemicarbazone (12.g) is added to 77 g. of ferric ammonium sulfate dodecahydrate in 500 ml. of water at 60° and the mixture is heated to 90°–100° for 4 hours. The mixture is cooled, the solid collected and washed with water. Only 0.92 g. (melting point 249°–251°) of product is soluble in a large volume of acetone. The remaining product is dissolved in 150 ml. of dimethylformamide, filtered and the filtrate evaporated to dryness to give a solid. This solid is treated with about 20 ml. of acetone, slurried, cooled and collected to give yellow crystals. After drying in an air stream overnight, 5.5 g. (melting point 253.5–255°) of 2-(2-amino-5-thiadiazolyl)-1-(2-hydroxyethyl)-5-nitroimadazole is obtained; no carbonyl absorption band is present in the infrared spectrum. Thus, it is not necessary to perform a separate hydrolysis step for the removal of the acetyl group.

EXAMPLE 9

Preparation of 2-(2-Dichloroacetamido-5-thiadiazolyl)-1-methyl-5-nitroimidazole

Five grams of 2-amino-5-(1-methyl-5-nitro-2-imidazolyl)-1,3,4-thiadiazole is added to 25 ml. of dichloroacetic anhydride, and the mixture boiled gently for a few minutes. After standing at room temperature for four hours, 200 ml. of diethyl ether is added, and the mixture stored at −10° C. overnight. The solid is collected, dried, and recrystallized from a mixture of 300 ml. of ethanol and 50 ml. of 2-methoxyethanol to yield 4.5 g. of pure product melting at 246°–247° C.

EXAMPLE 10

Preparation of 2-(2-Amino-5-oxadiazolyl)-1-methyl-5-nitroimidazole

Method A

In 180 ml. of hot water, 9.3 grams (0.06 mole) of 1-methyl-5-nitro-2-imidazolecarboxaldehyde is slurried while 6.7 grams (0.06 mole) of semicarbazide hydrochloride is added portionwise. After 15 minutes of heating, the mixture is cooled in a refrigerator overnight. The solid is then collected and washed with water and methanol, respectively, to give a yellow product, melting point 272°–273° C. (dec.). After drying at 100° for 2 hours under reduced pressure, 11.94 grams of 1-methyl-5-nitro-2-imidazolecarboxaldehyde semicarbazone is formed. This semicarbazone (6.35 grams or 0.03 mole) is added to 10 grams of anhydrous sodium acetate in 50 ml. of glacial acetic acid and 1.25 ml. of bromine is added with continuous stirring. The mixture is heated gradually to give a nearly clear red solution at 50° C. which becomes increasingly turbid with time. After heating at 75 ± 3° for 3 hours, the mixture is cooled and poured on ice. The yellow solid is collected, washed with water, then with methanol, and dried under reduced pressure at 70° C. for 3 hours to give 5 grams of crude 2-amino-5-(1-methyl-5-nitro-2-imidazolyl)-oxadiazole, melting point 284°–287° C. (dec.). This material is dissolved in boiling dimethylformamide, ethanol added, and the mixture cooled to give yellow crystals, melting point 291°–293° C. (dec.).

METHOD B

In 25 ml. of methanol, 0.93 grams (5 mmole) of 1-methyl-5-nitro-2-imidazolecarboxylic acid hydrazide and 0.53 grams (5 mmole) of cyanogen bromide are refluxed for 2 hours, cooled, and poured on ice to give a pale yellow solid. This solid is collected, washed with water, and dried under reduced pressure at 100° C. for 2 hours to give 0.65 grams, melting point 286°–288° C. (dec.), of 2-amino-5-(1-methyl-5-nitro-2-imidazolyl-)oxadiazole.

EXAMPLE 11

Preparation of 2-(2-Methylamino-5-oxadiazolyl)-1-methyl-5-nitroimidazole

To a solution of 8.5 grams (0.055 mole) of 1-methyl-5-nitro-2-imidazolecarboxaldehyde in 50 ml. of ethanol is added a solution of 5.0 grams (0.056 mole) of 4-methylsemicarbazide in 25 ml. of ethanol and 10 ml. of water containing 2-4 drops of concentrated hydrochloric acid. The resulting solution is heated at 60°–70° C. until a yellow solid starts to separate and then stored at 0° C. for 1 hour; 12.2 grams (98%) of 1-methyl-5-nitro-2-imidazolecarboxaldehyde-4-methylsemicarbazone is obtained melting at 221°–223° C.

Seven grams (0.031 mole) of 1-methyl-5-nitro-2-imidazolecarboxaldehyde-4-methylsemicarbazone is dissolved in 85 ml. of glacial acetic acid, 16 grams of anhydrous sodium acetate added, and a solution of 2.5 ml. of bromine in 20 ml. of glacial acetic acid added. The resulting mixture becomes a clear solution as it is heated at 70°–80° C. for 2-4 hours. The solvent is evaporated under reduced pressure and the residue treated with shaved ice until a yellow suspension is obtained. The product is collected, washed with cold water, methanol, and finally with ether. Recrystallization from ethanol containing N,N-dimethylformamide affords 2.7 grams (39%) of a yellow product melting at 239°–241° C. In another preparation, a 63% yield of product melting at 237°–239° C. is obtained without recrystallization.

EXAMPLE 12

Preparation of
2-(2-Dimethylamino-5-oxadiazolyl)-1-methyl-5-nitroimidazole

A solution of 780 mg. (5 millimoles) of 1-methyl-5-nitro-2-imidazolecarboxaldehyde in 10 ml. 95% of ethanol is treated with 520 mg. (5 millimoles) of 4,4-dimethylsemicarbazide and one drop of concentrated hydrochloric acid to give a yellow solid. The mixture is heated at 40° C. for 5 minutes, cooled to 0° C., and 1180 mg. (98%) of crystalline 1-methyl-5-nitro-2-imidazolecarboxaldehyde 4,4-dimethylsemicarbazone is obtained. Recrystallization from ethanol containing N,N-dimethylformamide affords 900 mg. (74%) of material melting at 206°–208° C.

The procedure of Method A of Example 10 is followed except that 7.5 grams (0.31 mole) of 1-methyl-5-nitro-2-imidazolecarboxaldehyde 4,4-dimethylsemicarbazone, prepared above, is used. The product is recrystallized from ethanol to give 5.2 grams (69%) of material melting at 180°–182° C.

EXAMPLE 13

Preparation of
2-(2-Acetamido-5-oxadiazolyl)-1-methyl-5-nitroimidazole

Four grams of acetyl chloride are slowly added to 3.6 grams (0.017 mole) of 2-(2-amino-5-oxadiazolyl)-1-methyl-5-nitroimidazole suspended in a mixture of 44 ml. of pyridine and 35 ml. of benzene. The addition is completed in 30 minutes, the mixture heated at 60°–70° C. for 10 minutes, and then poured into 500 ml. of ice and water. After the resulting mixture is stirred for 1 ½ hours, the product separates. Recrystallization from 150 ml. of acetone containing some N,N-dimethylformamide affords 2.4 grams (56%) of pale yellow product. A second recrystallization from acetone gives 2.1 g. of product, melting point 224°–225° C.

EXAMPLE 14

Preparation of
2-{2-[(Dimethylaminomethylene)amino]-5-thiadiazolyl}-1-methyl-5-nitroimidazole Phosgene gas is bubbled into 100 ml. of N,N-dimethylformamide at 5°–10° C. until 2.0 g. (0.02 mole) is absorbed and a crystalline suspension is formed. This suspension is added in portions to a stirred mixture of 4.5 g. (0.02 mole) of 2-(2-amino-5-thiadiazolyl)-1-methyl-5-nitroimidazole and 100 ml. of N,N-dimethylformamide at 25° C. After 30 minutes the reaction mixture is diluted with 200 ml. of diethyl ether, and the pale yellow solid is collected, washed with ether, and dried. Treatment of this material with 150 ml. of water and drying affords 5.0 g. (89%) of brilliant yellow solid melting at 230°–232° C.

EXAMPLE 15

Preparation of
2[2-(4-Carbethoxy-1-piperazinyl)-5-thiadiazolyl]-1-methyl-5-nitroimidazole The compound 1-methyl-5-nitro-2-imidazole carboxaldehyde-4-carbethoxy-1-piperazine thiocarbohydrazone is prepared by the procedure of Example 3, 23.2 gm., 0.1 mole, of 4-carbethoxypiperazine-1-thiocarbohydrazide replacing the 4,4-dimethyl-3-thiosemicarbazide. The yield is 8.6 gm. and the melting point 182°–183° C.

A suspension of 6.4 gm., 0.0174 mole, of 1-methyl-5-nitro-2-imidazolecarboxaldehyde-4-carbethoxy-1-piperazine thiocarbohydrazone (prepared above) in 200 ml. of boiling ethanol is stirred as a solution of 35 mg. of ferric ammonium sulfate dodecahydrate in 200 ml. of hot water is added in one portion. A deep red-brown solution results. After stirring and heating on the steam bath for 4 hours, a precipitate is present. This is collected, washed with water, dried and recrystallized from hot ethanol to give 3.6 grams of the title compound melting at 179°–181° C.

EXAMPLE 16

Preparation of
2-[2-(Hydroxyethylamino)-5-thiadiazolyl]-1-methyl-5-nitroimidazole A solution of 1.3 gm., 0.0058 mole, of 2-(2-amino-5-thiadiazolyl)-1-methyl-5-nitroimidazole is dissolved in 25 ml. of concentrated hydrochloric acid, cooled to 5° C., stirred, and treated during five minutes with a solution of 0.5 gm., 0.0073 mole, of sodium nitrite in 2 ml. of water. The mixture is kept at room temperature for 18 hours. The precipitate present is collected, washed with water, dried and then extracted with warm acetone. Removal of the acetone leaves a solid residue which is recrystallized from a mixture of acetone and diethylether to give 0.16 gm. of 2-(2-chloro-5-thiadiazolyl)-1-methyl-5-nitroimidazole as yellow crystals, melting at 135°–137° C.

A mixture consisting of 4.9 gm., 0.02 mole, of 2-(2-chloro-5-thiadiazolyl)-1-methyl-5-nitroimidazole, 3.0 gm., 0.05 mole, of ethanolamine, and 50 ml. of p-dioxane is stirred at room temperature for twenty-four hours. The precipitate is collected, washed with aqueous sodium bicarbonate solution, dried and recrystallized from methanol to give the pure compound melting at 208°–209° C. Working up the mother liquors gives additional material, the total yield being 3.4 gm.

EXAMPLE 17

Preparation of 2-[2-(3-Dimethylaminopropylamino)-5-thiadiazolyl]-1-methyl-5-nitroimidazole A mixture consisting of 3.8 gm., 0.0155 mole of 2-(2-chloro-5-thiadiazolyl)-1-methyl-5-nitroimidazole, prepared as in Example 16 2.5 gm., 0.029 mole of 3-dimethylaminopropylamine, 2.1 gm. 0.025 mole, of sodium bicarbonate and 100 ml. of benzene is refluxed for 22 hours. The reaction mixture is cooled to room temperature, washed with aqueous sodium bicarbonate and sodium chloride solutions. Cooling to 5° C. gives a crystalline precipitate which is collected and recrystallized from benzene to give the pure compound melting at 153°–154° C. More product is obtained from the mother liquors to give an overall yield of 3.0 gm.

EXAMPLE 18

Preparation of
2-(2-Amino-5-oxadiazolyl)-1-(2-hydroxyethyl)-5-nitroimidazole,
2-(2-methylamino-5-oxadiazolyl)-1-(2-hydroxyethyl)-5-nitroimidazole, and
2-(2-dimethylamino-5-oxadiazolyl)-1-(2-hydroxyethyl)-5-nitroimidazole 1-(2-hydroxy)-5-nitro-2-imidazolecarboxaldehyde (1 mole) is treated with 1 mole of semicarbazide hydrochloride in ethanol to give nearly a quantitative yield of semicarbazone. The product is treated with bromine and sodium acetate in the manner described in Method A of Example 1 to give the first compound above which melts with decomposition at 228°–230° C.

The use of 4-methylsemicarbazide and 4,4-dimethylsemicarbazide hydrochlorides instead of semicarbazide hydrochloride, followed by treatment of the methylated semicarbazones with bromine and sodium acetate as above, gives, respectively, 2-(2-methylamino-5-oxadiazolyl)-1-(2-hydroxyethyl)-5-nitroimidazole, melting at 202.5°–204° C., and 2-(2-dimethylamino-5-oxadiazolyl)-1-(2-hydroxyethyl)-5-nitroimidazole, melting at 171°–173° C.

EXAMPLE 19

Preparation of 2-(2-Amino-5-thiadiazolyl)-1-(2-acetoxyethyl)-5-nitroimidazole

The sample (0.1 g.) of 2-amino-5-[1-(2-hydroxyethyl)-5-nitro-2-imidazolyl]thiadiazole is dissolved in 2 ml. of hot glacial acetic acid and a drop of concentrated sulfuric acid is added. The solution is refluxed for 45 minutes, cooled and poured on ice to give a yellow solid. This solid is collected, washed with water and dried; the yield is 0.1 g., melting point 159°–162° C. (turbid). A purified sample of the 2-amino-5-[1-(2-acetoxyethyl)-5-nitro-2-imidazolyl]thiadiazole, melts at 164°–165.5° C.

EXAMPLE 20

Preparation of 2-(2-Acetamido-5-thiadiazolyl)-1-(2-acetoxyethyl)-5-nitroimidazole The sample (0.1 g.) of 2-amino-5-[1-(2-hydroxyethyl)-5-nitro-2-imidazolyl]thiadiazole is added to 1.5 ml. of acetic anhydride and heated under reflux for 20 minutes. After cooling, the mixture is evaporated to dryness to give a tan solid which is slurried with ether and collected, melting point 258°–265° C.; the yield is 0.11 g. This solid is recrystallized from acetone to give the purified product, melting point 264°–268° C.

EXAMPLE 21

Preparation of 2-(2-Amino-5-thiadiazolyl)-1-methyl-5-nitroimidazole Hydrochloride Four grams of 2-(2-amino-5-thiadiazolyl)-1-methyl-5-nitroimidazole is added to concentrated hydrochloric acid. The resultant precipitate of the hydrochloride is filtered off and air dried; melting point 249° C. with decomposition. When the hydrochloride is added to water, the free base is formed again without the necessity of using alkali.

EXAMPLE 22

Preparation of 2-(2-Hydroxymethylamino-5-thiadiazolyl)-1-methyl-5-nitroimidazole A suspension of 5 g. of 2-(2-amino-5-thiadiazolyl)-1-methyl-5-nitroimidazole in 200 ml. of 36% aqueous formaldehyde solution is stirred for 20 hours at room temperature. The suspension is cooled in ice, and the insoluble solid is collected by filtration and washed with acetone. The yield of the title compound is 6.15 g., melting point 177° C. with decomposition (rapid heating).

EXAMPLE 23

Preparation of 2-(2-Amino-5-thiadiazolyl)-1-ethyl-5-nitroimidazole

A slurry of β-(1-ethyl-5-nitro-2-imidazolyl)styrene (42.7 g. or 0.175 mole) in 350 ml. of methanol containing 14.6 ml. of water at 25° C. is treated with ozone until a nearly clear, pale-yellow solution is obtained. Subsequently, the mixture is treated with 42 g. of sodium iodide in 138 ml. of water and 20.3 ml. of glacial acetic acid at 25° C. The mixture is stirred for 40 minutes and 44.1 g. (0.288 mole) of sodium thiosulfate in 242 ml. of water added. The mixture is filtered, and the filtrate concentrated at 70°–75° C. under 15–20 mm. of pressure to give 450 ml. of solution. The solution is acidified with 50 ml. of 6N hydrochloric acid and the benzaldehyde removed at 70°–75° C. under 15–20 mm. of pressure. The residue is then neutralized with saturated sodium bicarbonate solution and extracted with ethyl acetate to give an 81.5% yield of solid aldehyde, melting point 61°–67° C. after stripping. A sublimed sample of the aldehyde melts at 68°–69° C. with softening at 65° C. When the aqueous ozonized solution, after benzaldehyde is removed, is treated with thiosemicarbazide and mineral acid or semicarbazide hydrochloride and heated, the 1-ethyl-5-nitro-2-imidazolecarboxaldehyde thiosemicarbazone, melting point 241° C., or semicarbazone, melting point 223°–226° C., is obtained. The compound β-(1-ethyl-5-nitro-2-imidazolyl)styrene is prepared by treating 1-ethyl-2-methyl-5-nitroimidazole with benzaldehyde in absolute ethanol and potassium tertiary butoxide in nitrogen atmosphere below 37° C. A sample purified from 95% ethanol melts at 136.5°–137.5° C.

A solution of 184 g. of ferric ammonium sulfate dodecahydrate in 680 ml. of water is heated to 60° C. and 23.1 g. of 1-ethyl-5-nitro-2-imidazolecarboxaldehyde thiosemicarbazone (prepared as above) is added with efficient stirring. The temperature is raised to 90° C. and vigorous stirring continued for 4 hours. The reaction mixture is cooled to 4° C. and filtered. The solid is washed with warm water and dried under vacuum at 110° C. and then extracted with 800 ml. of hot acetone, followed by three 300-ml. portions of hot acetone. Cooling the acetone gives a solid product, which is filtered off; melting point 231°–233° C. A second crop with the same melting point is obtained by evaporating the filtrate and recrystallizing the residue from acetone. The combined yield is 17.0 g. (74.5%).

EXAMPLE 24

Preparation of
2-(2-Amino-5-thiadiazolyl)-1-benzyl-5-nitroimidazole 0.5 g. (1.64 millimole) of β-(1-benzyl-5-nitro-2-imidazolyl)styrene in 95% aqueous methanol is treated with ozone until a clear solution is obtained. To this solution at 15° C., 0.312 g. (1.64 millimole) of sodium meta-bisulfite ($Na_2S_2O_5$) in 3 ml. of water is added. The mixture is then evaporated to dryness under reduced pressure at 75° C. and the solid extracted with ethyl acetate. The ethyl acetate extracts are dried, evaporated to dryness to give a yellow-orange residue (probably bisulfite addition product) which solidifies upon standing. This material is dissolved in 20 ml. of aqueous methanol and 0.15 g. of thiosemicarbazide and a drop of 6N hydrochloric are added. After refluxing for 15 minutes and cooling, 0.25 g., melting point 193°–196° C., of 1-benzyl-5-nitro-2-imidazolecarboxaldehyde thiosemicarbazone is isolated. The use of a half of an equimolar amount of sodium meta-bisulfite affords the title aldehyde instead of the bisulfite addition product. When the ethyl acetate extract is evaporated to dryness and dissolved in 75% aqueous ethanol and semicarbazone is added, and the mixture is heated on a steam bath for 10 minutes, and sodium acetate is added, the semicarbazone derivative, melting point 226°–228° C. is obtained. Twelve grams of 1-benzyl-5-nitro-2-imidazolecarboxaldehyde thiosemicarbazone are added to a stirred solution of 76.2 g. of ferric ammonium sulfate dodecahydrate in 600 ml. of water at 50° C. and the slurry is heated at 90°–95° C. for 6 hours. The mixture is cooled in ice and the yellow-brown solid collected, washed with water, and dried under pressure. The yield of product is 10.9 g. Recrystallization from methanol gives analytically pure material melting at 213°–215° C.

EXAMPLE 25

Preparation of
2-(2-Amino-5-oxadiazolyl)-1-ethyl-5-nitroimidazole

A slurry of 10.2 g. of 1-ethyl-5-nitro-2-imidazolecarboxaldehyde semicarbazone (prepared as in Example 23), and 15.0 g. of anhydrous sodium acetate in 75 ml. of glacial acetic acid is treated with 1.87 ml. of bromine at 81° C. under agitation. Stirring is continued at 75°–80° C. for 17½ hours, at which time workup of a sample shows starting material still present. An additional 7.5 g. of sodium acetate and 1.00 ml. of bromine are added and stirring continued for 3 hours. A final 3.85 g. of sodium acetate and 0.50 ml. of bromine are added and the reaction mixture is stirred for 1 hour at 75° C. The reaction mixture is cooled to 15° C. and poured over ice. The product is filtered off, washed with water and dried under reduced pressure. The yield is 6.3 g. and the melting point 265° C. with decomposition.

EXAMPLE 26

Preparation of
2-(2-Amino-5-oxadiazolyl)-1-benzyl-5-nitroimidazole

A slurry of 6.1 g. of 1-benzyl-5-nitro-2-imidazolecarboxaldehyde semicarbazone (prepared as in Example 24) and 8 g. of anhydrous sodium acetate in 40 ml. of glacial acetic acid is stirred at 40° C. while 3.4 g. of bromine in 15 ml. of acetic acid is slowly added. The mixture is heated at 65°–70° C. for 4 hours, then poured on ice and the yellow solid collected, washed with water, and dried under pressure. The yield is 5.7 g. Recrystallization from acetone gives analytically pure material melting at 261.5°–262.5° C.

EXAMPLE 27

Preparation of
2-[2-(2,2-Diethoxyethylamino)-5-thiadiazolyl]-1-methyl-5-nitroimidazole A mixture composed of 9.8 g. of 2-(2-chloro-5-thiadiazole)-1-methyl-5-nitroimidazole, (Example 16), 11.0 g. of 2,2-diethoxyethylamine, and 250 ml. of dioxane is stirred and heated on the steam bath for 12 hours. It is then diluted with 500 ml. of cold water, cooled, and the precipitated yellow solid collected and dried. Recrystallization from 50% aqueous ethanol gives the pure compound melting at 154°–155° C.

EXAMPLE 28

Preparation of
2-(2-Piperidino-5-thiadiazolyl)-1-methyl-5-nitroimidazole

A mixture composed of 7.4 g. of 2-(2-chloro-5-thiadiazolyl)-1-methyl-5-nitroimidazole (Example 16), 6 g. of piperidine, and 200 ml. of dioxane is stirred at room temperature for 24 hours, and then taken to dryness under reduced pressure. The residue is shaken with 100 ml. of water and the insoluble portion collected and dried. Recrystallization from 150 ml. of 2-methoxyethanol gives 7.6 g. of the subject compound melting at 212°–213° C.

EXAMPLE 29

Preparation of
2-(2-n-Hexylamino-5-thiadiazolyl)-1-methyl-5-nitroimidazole

The preparation of the title compound is carried out essentially as described for the 2-piperidino derivative (Example 28), 6.5 g. of n-hexylamine replacing the piperidine. The crude product is recrystallized from 125 ml. of 2-methoxyethanol to give 5.2 g. of the pure compound melting at 146°–147° C.

EXAMPLE 30

Preparation of
2-[4-(2-Hydroxyethyl)-1-piperazinyl-5-thiadiazolyl]-1-methyl-5-nitroimidazole The preparation of the subject compound is carried out essentially as described for the 2-piperidino derivative (Example 28), 3.9 g. of 1-(2-hydroxyethyl)piperazine replacing the piperidine. After recrystallization

EXAMPLE 31

Preparation of
2-{2-[4-(3-Dimethylaminopropyl)-1-piperidino]-5-thiadiazolyl}-1-methyl-5-nitroimidazole The preparation of the title compound is carried out by the procedure described for the 2-piperidino derivative (Example 28), 5.1 g. of 4-(3-dimethylaminopropyl)piperidine replacing the piperidine. Recrystallization from methanol gives 5.6 g. of pure product, melting at 174°–175° C.

EXAMPLE 32

Preparation of
2-{2-N-(2-Hydroxyethyl)methylamino]-5-thiadiazolyl}-1-methyl-5-nitroimidazolo The preparation of the above compound is carried out essentially as described for the 2-piperidino derivative (Example 28), an equivalent of N-methylethanolamine replacing the piperidine. The pure compound melts at 158°–160° C. after recrystalliation from methanol.

EXAMPLE 33

Preparation of
2-[2-(1-Piperazinyl)-5-thiadiazolyl]-1-methyl-5-nitroimidazole

The preparation of the subject compound is carried out essentially as described for the 2-piperidino derivative (Example 28), two equivalents of piperazine replacing the piperidine. The crude product is recrystallized from 2-methoxyethanol to yield the pure compound melting at 240°–241° C.

EXAMPLE 34

Preparation of
2-[2-(4-Methyl-1-piperazinyl)-5-thiadiazolyl)-1-methyl-5-nitroimidazole The preparation of the above compound is carried out in the manner described for the 2-piperidino derivative (Example 28), an equivalent of 1-methylpiperazine replacing the piperidine. The crude product is purified by recrystallization from 2-methoxyethanol and melts at 242°–244° C.

EXAMPLE 35

Preparation of
2-{2-[4-(3-Dimethylaminopropyl)-1-piperazinyl]-5-thiadiazolyl}-1-methyl-5-nitroimidazole A solution of 2-(2-chloro-5-thiadiazolyl)-1-methyl-5-nitroimidazole in 200 ml. of dioxane is treated with 5.1 g. of 1-(3-dimethylaminopropyl)piperazine, and the mixture stirred at room temperature for 18 hours. The precipitate is collected, dissolved in 100 ml. of water, made alkaline with sodium hydroxide solution, and then extracted with 500 ml. of chloroform. The chloroform extract is dried and the solvent removed under reduced pressure. The yellow residue is recrystallized from 100 ml. of ethanol to give 2.9 g. of product, melting at 174°–175° C.

EXAMPLE 36

Preparation of
2-{2-[4-(2-Pyridyl)-1-piperazinyl]-5-thiadiazolyl}-1-methyl-5-nitroimidazole The preparation of the above compound is carried out essentially as described for the 2-[4-(3-dimethylaminopropyl)-1-piperazinyl derivative] (Example 35), an equivalent of 1-(2-pyridyl)piperazine replacing the 1-(3-dimethylaminopropyl)piperazine. After recrystallization from 2-methoxyethanol, the pure compound melts at 280°–282° C.

EXAMPLE 37

Preparation of
2-{2-[4-(2-Thiazolyl)-1-piperazinyl]-5-thiadiazolyl}-1-methyl-5-nitroimidazole The preparation of the subject compound is carried out essentially as described for the 2-[4-(3-dimethylaminopropyl)-1-piperazinyl] derivative (Example 35), an equivalent of 1-(2-thiazolyl)piperazine replacing the 1-(3-dimethylaminopropyl)piperazine. After recrystallization from 2-methoxyethanol, the pure compound melts at 297°–300° C.

EXAMPLE 38

Preparation of
2-(2-Cyclohexylamino-5-thiadiazolyl)-1-5-nitroimidazole

A mixture of 5.0 g. of 2-(2-chloro-5-thiadiazolyl)-1-methyl-5-nitroimidazole, 6.0 g. of cyclohexylamino and 125 ml. of dioxane is stirred at reflux until thin-layer chromatographic analysis indicates that the chloro intermediate is completely utilized. The dioxane is removed under pressure and the residue triturated with aqueous sodium bicarbonate solution. Recrystallization from a mixture of ethylacetate and acetone yields the pure compound melting at 215°–217° C.

EXAMPLE 39

Preparation of
2-(2-t-Butylamino-5-thiadiazolyl)-1-methyl-5-nitroimidazole

The preparation of the above compound is accomplished essentially by the procedure described for the 2-cyclohexylamino derivative (Example 38), as equivalent of t-butylamine replacing the cyclohexylamine. Recrystallization of the crude product from a mixture of ethyl acetate and acetone gives the pure compound melting at 249°–251° C.

EXAMPLE 40

Preparation of
2-(2-n-Octylamino-5-thiadiazolyl)-1-methyl-5-nitroimidazole

The preparation of the above compound is carried out essentially as described for the 2-cyclohexylamino derivative (Example 38), an equivalent of n-octylamine replacing the cyclohexylamine. The crude product is purified by recrystallization from aqueous 2-methoxyethanol and then melts at 130°–132° C.

EXAMPLE 41

Preparation of 2-(2-Chloroacetamido-5-thiadiazolyl)-1-methyl-5-nitroimidazole

Twenty grams of 2-(2-amino-5-thiadiazolyl)-1-methyl-5-nitroimidazole is added in portions to a solution of 60 g. of chloroacetic anhydride in 250 ml. of dioxane at 90°–95° C. The mixture is stirred at this temperature for 3 hours. After standing at room temperature, the mixture is filtered and precipitate washed with diethyl ether and dried. Recrystallization from 2-methyloxyethanol gives the pure compound, melting at 239°–240° C. with decomposition.

EXAMPLE 42

Preparation of 2-(2-Morpholinoacetamido-5-thiadiazolyl)-1-methyl-5-nitroimidazole Six grams of 2-(2-chloroacetamido-5-thiadiazolyl)-1-methyl-5-nitroimidazole (Example 42) is added to a solution of 4 grams of potassium iodide in 2 liters of anhydrous acetone, and the mixture then influxed for 2 hours. Potassium chloride precipitates from the solution. Four grams of morpholine is added and the mixture refluxed for 7 hours. The solvent is removed in a stream of air. The residual solid is slurried with 100 ml. of water, filtered, and dried. Recrystallization from 300 ml. of boiling dioxane gives 3.8 g. of the title compound, melting at 250°–252° C. with decomposition.

EXAMPLE 43

Preparation of 2-(2-Amino-5-thiazolyl)-1-propyl-5-nitroimidazole

The procedure of Example 23, with the substitution of β-(1-propyl-5-nitro-2-imidazolyl)styrene for β-(1-ethyl-5-nitro-2-imidazolyl)styrene in the first step is utilized to prepare 2-(2-amino-5-thiadiazolyl)-1-propyl-5-nitroimidazolo, melting at 234.5°–236° C.

EXAMPLE 44

Preparation of Chick Diet

The following feed composition is employed in all the the poultry experiments hereinafter set forth except where otherwise stated:

|  |  |
|---|---|
| Vitamin Pre-Mix | 0.5 % |
| Trace Minerals | 0.1 % |
| Sodium Chloride | 0.3 % |
| Dicalcium Phosphate | 1.2 % |
| Ground Limestone | 0.5 % |
| Stabilized Fat | 4 % |
| Dehydrated Alfalfa, 17% | 2 % |
| Corn Gluten Meal, 41% | 5 % |
| Menhaden Fish Meal, 60% | 5 % |
| Soybean Oil Meal, 44% | 30 % |
| Ground Yellow Corn, Fine | To 100 % |

The vitamin pre-mix in the above feed composition is prepared from the followng formulation. The expressions of quantity relate to units per kilogram of the feed composition.

|  |  |
|---|---|
| Butylated Hydroxy Toluene | 125 mg. |
| dl-Methione | 500 mg. |
| Vitamin A | 3300 I.U. |
| Vitamin D$_3$ | 1100 I.U. |
| Riboflavin | 4.4 mg. |
| Vitamin E | 2.2 I.U. |
| Niacin | 27.5 mg. |
| Pantothenic Acid | 8.8 mg. |
| Choline Chloride | 500 mg. |
| Folic Acid | 1.43 mg. |
| Menadione Sodium Bisulfate | 1.1 mg. |
| Vitamin B$_{12}$ | 11 mcg. |
| Ground Yellow Corn, Fine | to 5 gm. |

EXAMPLE 45

Utilization of compounds of the present invention in controlling colibacillosis

This example demonstrates the effectiveness of 2-(2-amino-5-thiadiazolyl)-1-methyl-5-nitroimidazole, 2-(2-acetamido-5-thiadiazolyl)-1-methyl-5-nitroimidazole, and other imidazoles in controlling colibacillosis in poultry.

Three groups of 10 five-day old sex-linked pullet chicks are infected parenterally, in the left thoracic air sac, with 0.2 ml. of a $10^{-1}$ dilution of a Trypticase Soy Broth culture of *Escherichia coli*, the causative agent of colibacillosis in poultry. The compounds to be tested are administered by gavage as a single oral dose in an aqueous solution or suspension, and the chicks are permitted to feed ad libitum the feed composition prepared in Example 44. Twelve days after treatment, the test is terminated and the number of survivors in each group recorded. The results are compared with two control groups of 20 chicks each, in which one control group is infected and untreated, and the second control group is uninfected and untreated. The results of the test are set forth in the following table.

TABLE I

| Compound | Dose* | Total Chicks Tested | Survivors |
|---|---|---|---|
| 2-(2-amino-5-thiadiazolyl)-1-methyl-5-nitroimidazole | 160 mg. | 10 | 10 |
|  | 80 mg. | 10 | 10 |
|  | 40 mg. | 10 | 10 |
| 2-(2-amino-5-oxadiazolyl)-1-methyl-5-nitroimidazole | 80 mg./kg. | 20 | 15 |
|  | 20 mg./kg. | 20 | 13 |
|  | 5 mg./kg. | 20 | 7 |
| 2-[2-(1-piperazinyl)-5-thiadiazolyl]-1-methyl-5-nitroimidazole | 160 | 20 | 18 |
|  | 40 | 20 | 6 |
| Control |  |  |  |
| Infected - Untreated |  | 20 | 2 |
| Uninfected - Untreated |  | 20 | 20 |

*Dose is in terms of milligrams per kilogram of body weight.

Four groups of 40, five-day old sex-linked pullet chicks are infected in the same manner as herein set forth with Escherichia coli. The compound 2-(2-acetamido-5-thiadiazolyl)-1-methyl-5-nitroimidaole is administered by gavage as a single oral dose in an aqueous medium, and the chicks are permitted to feed ad libitum the feed composition prepared in Example 44. Twelve days after treatment, the test is terminated and the number of survivors in each group recorded. The results are compared with two control groups of 40 chicks each, in which one control group is infected and untreated, and the second control group is uninfected and untreated. The results of the test are set forth in the following table.

TABLE II

| Compound | Dose* | Total Chicks Tested | Survivors |
|---|---|---|---|
| 2-(2-acetamido-5-thiadiazolyl)-1-methyl-5-nitroimidazole | 40 mg. | 40 | 39 |
| | 20 mg. | 40 | 35 |
| | 10 mg. | 40 | 29 |
| Control | | | |
| Infected - Untreated | | 40 | 3 |
| Uninfected - Untreated | | 40 | 40 |

*Dose is in terms of milligrams per kilogram of body weight.

EXAMPLE 46

Utilization of compounds of the present invention in controlling fowl typhoid

This example demonstrates the effectiveness of the compounds of this invention.

Groups of five one-day old sex-linked pullet checks are infected orally by gavage with 0.5 ml. of a $10^{-2}$ dilution of a five-hour Trypticase Soy Broth culture of *Salmonella gallinarum*, the causative agent of fowl typhoid. Each chick receives approximately $6 \times 10^5$ viable cells. Medication is administered continuously in the feed, beginning 3 hours before infection and continuing for 10 days, at which time the test is terminated and the number of survivors in each group recorded. Each test utilizes two control groups of chicks, the first group comprising 20 chicks which are infected and untreated, and the second group comprising 10 chicks which are uninfected and untreated. The results of the tests are set forth in the following Table III (in some instances, the results from two or more tests are combined):

TABLE III

| Compound | Dose* | Total Chicks Tested | Survivors |
|---|---|---|---|
| 2-(2-Amino-5-thiadiazolyl)-1-nitroimidazole | 0.1% | 10 | 9 |
| | 0.05% | 5 | 5 |
| | 0.025% | 5 | 5 |
| | 0.006% | 5 | 1 |
| 2-(2-Acetamido-5-thiadiazolyl)-1-methyl-5-nitroimidazole | 0.1% | 5 | 5 |
| | 0.025% | 5 | 4 |
| | 0.006% | 5 | 3 |
| 2-(2-Methylamino-5-thiadiazolyl)-1-methyl-5-nitroimidazole | 0.1% | 5 | 3 |
| 2-(2-Dimethylamino-5-thiadiazolyl)-1-methyl-5-nitroimidazole | 0.1% | 5 | 4 |
| 2-(2-Amino-5-thiadiazolyl)-1-ethyl-5-nitroimidazole | 0.1% | 10 | 10 |
| | 0.025% | 10 | 9 |
| 2-(2-Amino-5-oxadiazolyl)-1-ethyl-5-nitroimidazole | 0.1% | 10 | 10 |
| | 0.025% | 5 | 5 |
| | 0.006% | 5 | 3 |
| 2-(2-Amino-5-thiadiazolyl)-1-benzyl-5-nitroimidazole | 0.1% | 10 | 10 |
| | 0.025% | 10 | 4 |
| 2-(2-Amino-5-oxadiazolyl)-1-benzyl-5-nitroimidazole | 0.1% | 10 | 9 |
| | 0.025% | 10 | 1 |
| | 0.006% | 10 | 1 |
| 2-(2-Hydroxymethylamino-5-thiadiazolyl)-1-methyl-5-nitroimidazole | 0.1% | 10 | 10 |
| | 0.025% | 10 | 2 |
| | 0.006% | 10 | 2 |
| 2-{2-[N-(2-Hydroxyethyl)methylamino]-5-thiadiazolyl}-1-methyl-5-nitroimidazole | 0.1% | 10 | 8 |
| 2-(2-Morpholinoacetamido-5-thiadiazolyl)-1-methyl-5-nitroimidazole | 0.1% | 10 | 10 |
| | 0.025% | 5 | 1 |
| 2-(2-Amino-5-thiadiazolyl)-1-methyl-5-nitroimidazole hydrochloride | 1.0% | 10 | 10 |
| | 0.025% | 5 | 3 |
| 2-[2-(4-Methyl-1-piperazinyl)-5-thiadiazolyl]-1-methyl-5-nitroimidazole | 0.1% | 10 | 4 |
| 2-(2-Ethylamino-5-thiadiazolyl)-1-methyl-5-nitroimidazole | 0.1% | 10 | 10 |
| | 0.025% | 10 | 3 |
| | 0.006% | 5 | 3 |
| 2-(2-Cyclohexylamino-5-thiadiazolyl)-1-methyl-5-nitroimidazole | 0.1% | 10 | 8 |
| 2-(2-t-Butylamino-5-thiadiazolyl)-1-methyl-5-nitroimidazole | 0.1% | 10 | 6 |
| 2-(2-n-Hexylamino-5-thiadiazolyl)-1-methyl-5-nitroimidazole | 0.1% | 10 | 6 |
| 2-(2-Piperidino-5-thiadiazolyl)-1-methyl-5-nitroimidazole | 0.1% | 10 | 4 |
| 2-[2-(1-Piperazinyl)-5-thiadiazolyl]-1-methyl-5-nitroimidazole | 0.1% | 10 | 8 |
| | 0.025% | 10 | 1 |
| 2-(2-amino-5-thiadiazolyl)-1-(2-hydroxyethyl)-5-nitroimidazole | 0.1% | 10 | 10 |
| | 0.025% | 10 | 8 |
| 2-[4-(2-Hydroxyethyl)-1-piperazinyl]-5-thiadiazolyl]-1-methyl-5-nitroimidazole | 0.1% | 10 | 7 |
| | 0.025% | 10 | 3 |
| 2-(2-Dichloroacetamido-5-thiadiazolyl)-1-methyl-5-nitroimidazole | 0.1% | 10 | 7 |
| | 0.025% | 15 | 3 |
| 2-{2-[(Dimethylaminomethylene)amino]-5-thiadiazolyl}-1-methyl-5-nitroimidazole | 0.1% | 5 | 5 |
| | 0.05% | 5 | 5 |
| 2-(2-Formamido-5-thiadiazolyl)-1-methyl-5-nitroimidazole | 0.1% | 10 | 5 |
| | 0.025% | 15 | 11 |
| | 0.006% | 15 | 9 |
| 2-(2-Amino-5-oxadiazolyl)-1-methyl-5-nitroimidazole | 0.1% | 10 | 10 |
| | 0.025% | 10 | 10 |
| | 0.006% | 10 | 9 |
| 2-(2-Dimethylamino-5-oxadiazolyl)-1-methyl-5-nitroimidazole | 0.1% | 10 | 9 |
| | 0.025% | 10 | 9 |
| | 0.006% | 10 | 2 |
| 2-(2-Acetamido-5-oxadiazolyl)-1-methyl-5-nitroimidazole | 0.1% | 10 | 10 |
| | 0.025% | 10 | 8 |
| 2-(2-Methylamino-5-oxadiazolyl)-1-methyl-5-nitroimidazole | 0.1% | 5 | 5 |
| | 0.025% | 10 | 10 |
| | 0.006% | 10 | 8 |
| 2-(2-Methylamino-5-oxadiazolyl)-1-(2-hydroxyethyl)-5-nitroimidazole | 0.1% | 10 | 6 |
| 2-(2-Dimethylamino-5-oxadiazolyl)-1-(2-hydroxyethyl)-5-nitroimidazole | 0.1% | 10 | 5 |
| | 0.025% | 10 | 2 |
| 2-(2-Amino-5-thiadiazolyl)-1-propyl-5-nitroimidazole | 0.1% | 10 | 6 |
| Control | | | |
| Infected - Untreated | | 20 | 0 |
| Uninfected - Untreated | | 10 | 10 |

*Dose is in terms of percentage by weight of the feedcomposition prepared in Example 45.

EXAMPLE 47

Utilization of composition of the present invention in controlling enteritis

This example demonstrates the effectiveness of 2-(2-amino-5-thiadiazolyl)-1-methyl and 1-ethyl-5-nitroimidazole in controlling enteritis.

Three groups of ten female Swiss Webster mice weighing 20 gm. are infected intraperitoneally with 0.5 ml. of $10^{-2}$ dilution of a five-hour Trypticase Soy Broth culture of *Salmonella choleraesuis* var. kunzendorf, the causitive agent of enteritis in pigs, an organism originally recovered from a field outbreak of Salmonella choleraesuis var. kunzendorf in pigs. Each mouse receives approximately $4.6 \times 10^7$ cells as the inoculating dose.

The mice are fed a medicated feed, which is a commercial mouse chow containing the compounds to be tested for 3 hours before the infection until 7 days after infection. The mice are held for an additional 7 days after the medication is stopped, and the number of survivors in each group recorded. The medicated feed is prepared by thoroughly admixing calculated amounts of the compounds with commercial mouse chow to provide essentially uniform distribution in the feed offered. The above results are compared with two control groups of ten mice each, in which one control group is infected and untreated, and the second control group is uninfected and untreated. The results of the test are set forth in the following table:

TABLE IV

| Compound | Dose* | Total Chicks Tested | Survivors |
|---|---|---|---|
| 2-(2-Amino-5-thiadiazolyl)-1-methyl-5-nitroimidazole | 0.1 % | 10 | 10 |
|  | 0.025% | 10 | 9 |
|  | 0.006% | 10 | 1 |
| 2-(2-Amino-5-thiadiazolyl)-1-ethyl-5-nitroimidazole | 0.1 % | 10 | 9 |
|  | 0.025% | 10 | 3 |
| Control |  |  |  |
| Infected - Untreated |  | 10 | 2 |
| Uninfected - Untreated |  | 10 | 10 |

*Dose is in terms of percentage by weight of the commercial mouse chow.

EXAMPLE 48

Experiments were conducted to determine the antibacterial activity of compounds of the present invention against *Proteus mirabilis*, *Staphylococus aureus* strain Smith and *Staphylococcus aureus* strain Rose a tetracycline-resistant strain of *Staphylococcus aureus*. Infection was initiated in Carworth Farms CFl-s female mice (body weight 18–22 mg.) by intra-abdominal infection of 0.5 ml. of the broth dilutions of 5 hour cultures of the above organisms. The results obtained are summarized in the following Tables V, VI, and VII.

TABLE V

Tests with *Proteus mirabilis*

| Compound | Dose mg./kg. | Results alive/tested |
|---|---|---|
| 2-(2-Amino-5-thiadiazolyl)-1-methyl-5-nitroimidazole | 128 | 30/30 |
| 2-(2-Methylamino-5-thiadazolyl)-1-methyl-5-nitroimidazole | 256 | 4/5 |
| 2-{2-[(Dimethylaminomethylene)amino]-5-thiadiazolyl}-1-methyl-5-nitroimidazole | 256 | 3/5 |
| 2-(2-Formamido-5-thiadiazolyl)-1-methyl-5-nitroimidazole | 128 | 20/20 |
| 2-(2-Amino-5-thiadiazolyl)-1-methyl-5-nitroimidazole hydrochloride | 128 | 7/10 |

The mortality among infected untreated controls in this test is usually at least 95%.

TABLE VI

Tests with *Staphylococcus aureus* strain Smith

| Compound | Dose mg./kg. | Results alive/tested |
|---|---|---|
| 2-(2-Amino-5-thiadiazolyl)-1-methyl-5-nitroimidazole | 64 | 16/20 |
| 2-(2-Methylamino-5-thiadiazolyl)-1-methyl-5-nitroimidazole | 128 | 4/5 |
| 2-[2-(4-Carbethoxy-1-piperazinyl)-5-thiadiazolyl]-1-methyl-5-nitroimidazole | 256 | 8/10 |
| 2-(2-Dimethylamino-5-thiadiazolyl)-1-methyl-5-nitroimidazole | 512 | 4/5 |
| 2-{2-[(Dimethylaminomethylene)amino]-5-thiadiazolyl}-1-methyl-5-nitroimidazole | 64 | 5/5 |
| 2-(2-Formamido-5-thiadiazolyl)-1-methyl-5-nitroimidazole | 64 | 5/5 |
| 2-(2-Amino-5-oxadiazolyl)-1-methyl-5-nitroimidazole | 128 | 9/10 |
| 2-(2-Acetamido-5-oxadiazolyl)-1-methyl-5-nitroimidazole | 128 | 3/5 |
| 2-(2-Methylamino-5-oxadiazolyl)-1-methyl-5-nitroimidazole | 128 | 3/5 |
| 2-(2-Amino-5-oxadiazolyl)-1-ethyl-5-nitroimidazole | 128 | 3/5 |
| 2-(2-Amino-5-thiadiazolyl)-1-methyl-5-nitroimidazole hydrochloride | 128 | 5/5 |
| 2-{2-[4-(3-Dimethylaminopropyl)-1-piperazinyl]-5-thiadiazolyl}-1-methyl-5-nitroimidazole | 256 | 3/5 |

The mortality among infected untreated controls in this test is usually at least 95%.

TABLE VII

Tests with *Staphylococcus aureus* strain Rose

| Compound | Dose mg./kg. | Results alive/tested |
|---|---|---|
| 2-(2-Amino-5-thiadiazolyl)-1-methyl-5-nitroimidazole | 128 | 10/10 |
| 2-(2-Methylamino-5-thiadazolyl)-1-methyl-5-nitroimidazole | 512 | 4/5 |
| 2-{2-[(Dimethylaminomethylene)amino]-5-thiadiazolyl}-1-methyl-5-nitroimidazole | 128 | 10/10 |
| 2-(2-Formamido-5-thiadiazolyl)-1-methyl-5-nitroimidazole | 512 | 5/5 |
| 2-(2-Amino-5-oxadiazolyl)-1-methyl-5-nitroimidazole | 512 | 5/5 |

TABLE VII-continued

Tests with *Staphylococcus aureus* strain Rose

| Compound | Dose mg./kg. | Results alive/tested |
|---|---|---|
| 2-(2-Dimethylamino-5-oxadiazolyl)-1-methyl-5-nitroimidazole | 512 | 5/5 |
| 2-(2-Methylamino-5-oxadiazolyl)-1-methyl-5-nitroimidazole | 128 | 5/5 |
| 2-(2-Amino-5-thiadiazolyl)-1-ethyl-5-nitroimidazole | 512 | 5/5 |
| 2-(2-Amino-5-oxadiazolyl)-1-ethyl-5-nitroimidazole | 512 | 5/5 |

The mortality among infected untreated controls in this test is usually 95% or more. Activity was also displayed by the compounds of this invention against the following organisms in mice: *E. coli, Salmonella typhosa, Klebsiella AD, Aerobacter aerogenes,* and *Streptococcus pyogenes* strain A (C 203).

EXAMPLE 49

This example demonstrates the effectiveness of the nitroimidazoles of this invention in controlling a Pasteurella multocida infection in mice Swiss Webster, female mice weighing 22±2 g. were infected by intrapeutoneal injection of 0.5 ml. of a 5 hour Trypticase Soy Broth culture containing $10^7$ cfu. of *P. multocida*. Each mouse was given by gavage at the time of infection 2 mg. of the test drug suspended in 0.2% agar. The number of mice surviving two weeks post-infection over the number of mice tested is recorded below for each compound. The results are shown in Table VIII.

TABLE VIII

| Compound | Survivors/Total mg./mouse | | | |
|---|---|---|---|---|
| | 2 | 1 | 0.5 | 0.25 |
| 2-(2-Amino-5-thiadiazolyl)-1-ethyl-5-nitroimidazole | 10/10 | | | |
| 2-(2-Amino-5-oxadiazolyl)-1-ethyl-5-nitroimidazole | 8/10 | | | |
| 2-(2-Amino-5-thiadiazolyl)-1-benzyl-5-nitroimidazole | 0/10 | | | |
| 2-(2-Hydroxymethylamino-5-thiadiazolyl)-1-methyl-5-nitroimidazole | 10/10 | | | |
| 2-{2-[N-(2-Hydroxyethyl)-methylamino]-5-thiadiazolyl}-1-methyl-5-nitroimidazole | 10/10 | 3/10 | 1/10 | |
| 2-(2-Morpholinoacetamido-5-thiadiazolyl)-1-methyl-5-nitroimidazole | 2/10 | | | |
| 2-(2-Ethylamino-5-thiadiazolyl)-1-methyl-5-nitroimidazole | 10/10 | | | |
| 2-{2-[4-(3-Dimethylaminopropyl)-1-piperazinyl]-5-thiadiazolyl}-1-methyl-5-nitroimidazole | 10/10 | | | |
| 2-(2-n-Hexylamino-5-thiadiazolyl)-1-methyl-5-nitroimidazole | — | 9/10 | 8/10 | 2/10 |
| 2-(2-Piperidino-5-thiadiazolyl)-1-methyl-5-nitroimidazole | — | 9/10 | 4/10 | 5/10 |
| 2-(2-Amino-5-oxadiazolyl)-1-(2-hydroxyethyl)-5-nitroimidazole | 10/10 | — | 9/10 | — |
| 2-{2-[4-(2-Thiazolyl)-1-piperazinyl]-5-thiadiazolyl}-1-methyl-5-nitroimidazole | 2/10 | | | |
| 2-[2-(1-Piperazinyl)-5-thiadiazolyl]-1-methyl-5-nitroimidazole | 1/10 | | | |
| 2-[4-(2-Hydroxyethyl)-1-piperazinyl-5-thiadiazolyl]-1-methyl-5-nitroimidazole | 10/10 | | | |
| 2-{2-[4-(3-Dimethylaminopropyl)-1-piperidino]-5-thiadiazolyl}-1-methyl-5-nitroimidazole | 10/10 | — | 9/10 | — |
| 2-(2-Amino-5-thiadiazolyl)-1-methyl-5-nitroimidazole | 64/70 | 145/160 | 160/179 | 87/50 |
| 2-{2-[(Dimethylaminomethylene)amino]-5-thiadiazolyl}-1-methyl-5-nitroimidazole | 10/10 | 28/30 | 39/40 | 32/40 |
| 2-(2-Formamido-5-thiadiazolyl)-1-methyl-5-nitroimidazole | 10/10 | 9/10 | 20/20 | 16/20 |
| 2-(Amino-5-thiadiazolyl)-1-(2-hydroxyethyl)-5-nitroimidazole | — | 20/20 | 18/20 | 23/30 |
| 2-(2-Amino-5-oxadiazolyl)-1-methyl-5-nitroimidazole | 14/20 | 8/20 | 3/20 | 2/20 |

Mortality among infected untreated controls in this experimental infection is usually at least 95%.

EXAMPLE 50

This example demonstrates the effectiveness of 2-(2-amino-5-thiadiazolyl)-1-methyl-5-nitroimidazole in controlling enteritis caused by *Salmonella choleraesuis* in swine.

In the late afternoon of the day before infection, feed is removed from all pens. The following morning each group receives 2.5 lbs. of feed mixed either with normal broth or broth containing *Salmonella choleraesuis* variety kunzendorf organisms. Most of this feed is consumed within an hour. For the rest of the trial the pigs are observed and graded daily. Five hours after infection the pigs are given normal feed or feed containing furazolidone, a known antisalmonella agent, or 2-(2-amino-5-thiadiazolyl)-1-methyl-5-nitroimidazole. Medicated feed is employed for 14 days after infection, at which time it is replaced with normal feed. The trial is terminated four weeks after infection. The results of this experiment are shown in Table IX.

TABLE IX

Mortality of Pigs Infected Via Feed with *Salmonella choleraesuis* var. *kunzendorf* and Medicated Via Feed for the First 14 Postinfection Days

| Drug | Drug Dose Ppm. in Diet | Mg./Kg. Per Day*a* | Survivors Per Total | Median Survival Time in Days |
|---|---|---|---|---|
| 2-(2-amino-5-thiadiazolyl)-1-methyl-5-nitroimidazole | 200 | 12.3 | 9/10* | — |
|  | 50 | 3.4 | 1/10 | 7.2 |
| Furazolidone | 200 | 7.5 | 2/10 | 10.0 |
|  | 50 | 2.1 | 0/10 | 6.8 |
| Infected-Untreated | — | — | 0/10 | 7.8 |
| Uninfected-Untreated | — | — | 10/10* | — |

*a*During first day postinfection.
*Differs significantly from infected-untreated group (P<.01).

EXAMPLE 51

The compound 2-(2-amino-5-thiadiazolyl)-1-methyl-5-nitroimidazole (Example 1) is active against both gram-negative and gram-positive organisms. In mice, it is rapidly absorbed, well tolerated and effective against lethal bacterial infections. In vitro, it is effective against gonococci and gram-negative bacilli. Its action is bactericidal.

In the following experimens both the base and the hydrochloride salt of 2-(2-amino-5-thiadiazolyl)-1-methyl-5-nitroimidazole are used. On a molar basis, they are equivalent in activity. In mice, the method used in this experiment has been described. (Redin, G. S., "Antibacterial activity in mice of minocyclin, a new tetracycline, " *Antimicrobial Agents and Chemotherapy*-1966, p. 371–376). Infections are initiated in Carworth Farms CF-1 female mice (body weight, 18 to 22 g.) by intra-abdominal injection of 0.5 ml. of the indicated broth dilutions of 5-hour cultures of the following organisms: Klebsiella pneumoniae AD, $10^{-4}$; *Salmonella typhosa* 6539, undiluted; *Escherichia coli* UC311, $10^{-3}$; Aerobacter aerogenes 75, $10^{-1}$; *Proteus mirabilis* 4671, $10^{-2}$; *Shigella flexneri* 2a M22-18, undiluted; *Streptococcus pyogenes* C203, $10^{-5}$; Staphylococcus aureus 3, undiluted; *S. aureus* Rose, undiluted; *S. aureus* 5, undiluted; *S. aureus* Smith, $10^{-2}$; and *Diplococcus pneumoniae* SVI, $10^{-6}$. For the *Neisseria meningitidis* N20 infection, 0.5 ml. of a 48-hour broth culture is used. Within 1 hour after infection, the mice are treated with drug suspended in 0.5 ml. of 0.2% aqueous agar administered by oral gavage. The drugs are tested at four to six dosage levels with 20 to 30 mice at each level. The results of replicate tests are pooled to determine the median effective dose ($ED_{50}$) by the procedure of Litchfield and Wilcoxon, 1949, a simplified method of evaluating dose-effect experiments, *J. Pharmacol. Exptl. Therap.* 96:99–113. Data are tiven in Table X hereinafter.

TABLE X

The compound 2-(2-amino-5-thiadiazolyl)-1-methyl-5-nitroimidazole tested against bacterial infections in mice (single oral dose)

| Infection*a* | Median effective dose (mg./kg.)*b* | |
|---|---|---|
| *Neisseria meningitidis* N20 | 0.2 | (0.1–0.5) |
| *Klebsiella pneumoniae* AD | 8 | (6–11) |
| *Salmonella typhosa* 6539 | 14 | (10–19) |
| *Escherichia coli* 311 | 16 | (12–21) |
| *Aerobacter aerogenes* 75 | 54 | (43–68) |
| *Proteus mirabilis* 4671 | 60 | (50–80) |
| *Shigella flexneri* 2a M22–18 | 89 | (52–150) |
| *Streptococcus pyogenes* C203 | 4 | (3–6) |
| *Staphylococcus aureus* 3 | 14 | (9–21) |
| *S. aureus* Rose | 28 | (18–44) |
| *S. aureus* 5 | 46 | (26–81) |
| *S. aureus* Smith | 56 | (40–77) |
| *Diplococcus pneumoniae* SVI | 69 | (53–90) |

*a*Mortality rate of the untreated infected control mice was >90% within 3 days. The experimental period was 14 days.
*b*Figures in parentheses indicate 95% confidence limits.

Concentrations of drug in plasma are determined by assay of blood obtained by heart puncture of noninfected mice. Blood samples (about 0.5 ml. per mouse) from 10 mice receiving the same dose of drug are pooled. The drug is assayed in the plasma by a standard agar-diffusion plate method with *Bacillus subtilis* (Lederle No. 17) as the test organism. Peak plasma drug concentrations are given in Table XI hereinafter where they are associated with the median effective dose.

TABLE XI

Peak concentrations of test compound *in plasma associated with median effective doses

| Infection | $ED_{50}$ (mg./kg.) | Peak concn. in plasma (ug/ml.) |
|---|---|---|
| *Neisseria meningitidis* N20 | 0.2 | <1 |
| *Streptococcus pyogenes* C203 | 4 | |
| *Klebsiella pneumoniae* AD | 8 | |
| *Salmonella typhosa* 6539 | 14 | |
| *Escherichia coli* 311 | 16 | 2–4 |
| *Staphylococcus aureus* 3 | 14 | |
| *Staphylococcus aureus* Rose | 28 | |
| *Staphylococcus aureus* 5 | 46 | |
| *Staphylococcus aureus* Smith | 56 | 6–12 |
| *Aerobacter aerogenes* 75 | 54 | |
| *Diplococcus pneumoniae* SV1 | 69 | |
| *Shigella flexneri* 2a M22–18 | 89 | 14–18 |
| *Proteus mirabilis* 4671 | 60 | |

*2-(2-amino-5-thiadiazolyl)-1-methyl-5-nitroimidazole.

EXAMPLE 52

The following organisms are used in an in vitro testing study involving the following species: *Neisseria gonorrhoeae* (36 strains), *N. meningitidis* (24), *Shigella flexneri* (II), *S. sonnei* (3), *Salmonella typhimurium* (5), *S. enteriditis* (1), *S. infantis* (1), *S. cholerasuis* (1), *S. organienburg* (1), *Salmonella* species not further identified (5), *E. coli* (24), *Enterobacter* (21 strains of *Klebisella pneumoniae* and *Aerobacter aerogenes*), *Proteus* sp., all indole-negative (20), *Pseudomonas* sp. (10), *D. pneumoniae* (10), *Streptococcus pyogenes* (15), *Staphy-* lococcus aureus (23), Streptococcus faecalis, enterocci (28). The media used are Nutrient Broth (Difco), Nutrient Agar, Nutrient Agar containing 5% defibrinated rabbit blood, or chocolate agar prepared by combining the following materials from BBL; GC medium base, hemoglobin, and enrichment supplement.

The effectiveness of the antibacterial agents against the clinical isolates is determined by the agar-dilution method. 2-(2-amino-5-thiadiazolyl)-1-methyl-5-nitroimidazole is relatively insoluble in water; therefore, a stock solution is prepared in dimethylsulfoxide (DMSO) and serially diluted in DMSO, then 0.1 ml. of dilution is mixed with 10 ml. of fluid agar. The concentration (1%) of DMSO did not affect the growth of the test cultures. The plates are inoculated with $10^{-3}$ dilutions of 5 hour broth cultures by means of a multiple inocula-replicator. (Steers, E., E. L. Foltz, and B. S. Graves, "An inocula replicating apparatus for routine testing of bacterial susceptibility to antibiotics," *Antibiot. Chemotherapy* 9:308–311 (1959). With meningococci and gonococci, 24- to 48-hour surface growth on chocolate agar is suspended in Trypticase Soy Broth (BBL) for reading of 40 to 50% transmittance at 530 nm in a Bausch and Lomb Spectronic-20 colorimeter; the cultures are then diluted 1,000-fold in broth. Inoculated plates are incubated at 37 C for 24 hours; meningococci and gonococci are incubated in an atmosphere of 5% carbon dioxide. The lowest concentration of drug that completely inhibited growth is recorded as the minimal inhibitory concentration.

For the comparison of inhibitory and killing concentrations, tests are performed in Nutrient Broth. A stock solution of the test compound in DMSO (5,120 ug/ml.) is diluted 1:40 in broth and sterilized by filtration through a 0.2-$\mu$m membrane filter (Millipore Corp., Bedford, Mass.). Twofold dilutions of the sterile broth solution are inoculated with equal volumes of $10^{-3}$ dilutions of a 5-hour broth culture and are incubated at 37° C. for 24 hours. Subcultures are made from all clear tubes by plating 0.1-ml. samples in duplicate and incubating the plates for 24 hours. The following Table XII summarizes the results.

TABLE XII

Activity of 2-(2-amino-5-thiadiazolyl)-1-methyl-5-nitroimidazole clinical isolates (agar-dilution method

| Organism | No. of Isolates Tested | Test Compound[a] |
|---|---|---|
| Gonococcus | 36 | 0.12 |
| Meningococcus | 24 | 1 |
| Shigella | 14 | 4 |
| Salmonella | 14 | 4 |
| E. coli | 24 | 8 |
| Enterobacter | 21 | 8 |
| Proteus | 20 | 64 |
| Pseudomonas | 10 | <128 |
| Diplococcus | 10 | 4 |
| Streptococcus Group A | 15 | 8 |
| Staphylococcus | 23 | 16 |
| Enterococcus | 28 | 64 |

[a]Drug concentration (ug/ml.) required to inhibit 90% of isolates

EXAMPLE 53

The efficacy of the compounds of the present invention for enhancing the growth rate and for improving feed efficiency of animals is shown in the following tests. Day-old chicks are divided into groups of ten birds each, five males and five females. These groups are then weighted, placed in pens and given free access to water and feed. The diet used is the same for both the test groups and the controls except that 100 ppm of 2-(2-amino-5-thiadiazolyl)-1-(2-hydroxyethyl)-5-nitroimidazole is admixed with the diet of the test groups. All feed is weighed such that an accurate determination as to the amount of gain per unit of feed can be ascertained.

All groups are weighed at 0 and 19 days after the test is begun and the data obtained are reported below. Table XIII, along with a description of the diet used.

TABLE XIII

| Supplement | No. Birds | Wt. in Grams Days 0 | Wt. in Grams Days 19 | Gain 19 Days | lb. feed lb. gain | % inc. over Controls Gain | % inc. over Controls F/G |
|---|---|---|---|---|---|---|---|
| None | 10 | 43 | 328.0 | 285 | 1.62 | | |
| None | 10 | 43.1 | 296.2 | 253 | 1.62 | | |
| None | 10 | 43.1 | 314.6 | 272 | 1.69 | | |
| None | 10 | 43.1 | 335.8 | 293 | 1.60 | | |
| Average | | 43.1 | 318.7 | 276 | 1.63 | | |
| 100 PPM 2-(2-amino-5-thiadiazolyl)-1-(2-hydroxyethyl)-5-nitroimidazole | | | | | | | |
| " | 10 | 43 | 352.2 | 309 | 1.53 | | |
| " | 9 | 43.2 | 327.8 | 285 | 1.52 | | |
| Average | | 43.1 | 340 | 297 | 1.525 | 7.6% | 6.5% |

DIET

| Ingredient | Concentration (%) |
|---|---|
| Ground yellow corn | 51.4 |
| Soybean oil meal (44%) | 30.0 |
| Corn gluten meal | 5.0 |
| Menhaden first meal (60%) | 5.0 |
| Fat (NRG-50) | 4.0 |
| Dehydrated alfalfa meal (17%) | 2.0 |
| Ground limestone (33% Ca) | 0.5 |
| Dicalcium phosphate | 1.2 |
| Sodium chloride | 0.3 |
| Trace minerals[1] | 0.1 |

DIET-continued

| Ingredient | Concentration (%) |
|---|---|
| Vitamin premix[2] | 0.5 |

[1]Lime Crest Z-2 Delamix which contains 25.5% calcium, 6.0% manganese, 2.0% iron, 2.0% zinc, 0.12% iodine and 0.02% cobalt.
[2]Provides 3300 I.U. Vitamin A, 1100 I.U. Vitamin D$_3$, 2.2 I.U. Vitamin E, 500 mg. choline chloride, 500 mg., DL-methionine, 125 mg. ethoxyquin, 27.5 mg. niacin, 8.8 mg. methionine, 125 mg. ethoxyquin, 27.5 mg. niacin, 8.8 mg. pantothenic acid, 4.4 mg. riboflavin, 1.43 mg. folic acid, 1.1 mg. menadione, 0.011 mg. Vitamin B$_{12}$ per kilogram of feed.

EXAMPLE 54

In the following tests, the same diet and procedure were used as described in Example 53 above, excepting that 10 ppm. of test compound was included in the diets of test groups.

Data obtained are reported in Table XIV below.

TABLE XIV

| Supplement | Number Birds | Weight in Grams Days 0 | 19 | Gain 19 Days | lb.feed/- lb. gain | % Increase Over Controls Gain | F/G |
|---|---|---|---|---|---|---|---|
| None | 10 | 40.5 | 323.5 | 283.0 | 1.57 | — | — |
| 2-(2-Amino-5-thiadiazolyl)-1-methyl-5-nitroimidazole | 10 | 40.6 | 339.7 | 299.1 | 1.47 | 6.0 | 6.8 |
| None | 10 | 41.9 | 332.0 | 290.1 | 1.52 | — | — |
| 2-(1-Methyl-5-nitro-2-imidazolyl)-5-piperidino-1,3,4-thiadiazole | 10 | 42.0 | 334.7 | 292.7 | 1.48 | 1.0 | 2.7 |
| None | 10 | 42.4 | 324.6 | 282.2 | 1.53 | — | — |
|  | 10 | 43.7 | 322.2 | 278.5 | 1.53 | — | — |
| 1-[5-(1-Methyl-5-nitro-2-imidazolyl)-1,3,4-thiadiazol-2-yl]-4-(2-thiazolyl)piperazine | 10 | 42.3 | 337.8 | 315.5 | 1.47 | 5.0 | 4.1 |
|  | 10 | 43.7 | 346.9 | 303.2 | 1.50 | 9.0 | 2.0 |
| None | 10 | 40.4 | 344.6 | 304.2 | 1.58 | — | — |
| N- 5-[1-(2-Hydroxyethyl)-5-nitro-2-imidazolyl]-1,3,4-thiadiazol-2-yl-acetamide | 10 | 40.4 | 345.9 | 305.5 | 1.57 | 0.7 | 0.6 |

EXAMPLE 55

Two experiments are conducted on commercial swine farms in Iowa to investigate the effects on daily gain and feed efficiency of young pigs from feeding various levels of 2-(2-amino-5-thiadiazolyl)-1-methyl-5-nitroimidazole in the ration. In each experiment, the pigs are weaned at approximately 4 weeks of age and placed on test immediately. The following experimental treatments are used:

A. Basal (Unmedicated ration)
B. Basal + Compound X (50 gm/ton of feed)
C. Basal + Compound X (100 gm/ton of feed)
D. Basal + Compound X (200 gm/ton of feed)
E. Basal + AUREO S.P. 250 (100 gm. of chlorotetracycline, 100 gm. of sulfamethazine and 50 gm. of penicillin/ton of feed).

Compound X = 2-(2-amino-5-thiadiazolyl)-1-methyl-5-nitroimidazole.

The composition of the basal ration fed is shown in Table XV. The length of these experiments is 42 days.

Results:

The average performance data for these two experiments is shown in Table XV. The daily gains for all three levels of 2-(2-amino-5-thiadiazolyl)-1-methyl-5-nitroimidazole are clearly superior to those for the unmedicated control pigs. The pigs receiving the two higher levels (100 and 200 grams per ton) gained more rapidly than those receiving the lower level (50 gm./ton). Treatment E (AUREO S.P. 250) is included in these experiments as a positive control.

A marked improvement in feed efficiency was obtained at all levels of 2-(2-amino-5-thiadiazolyl)-1-methyl-5-nitroimidazole fed.

TABLE XV

| Basal Swine Ration | |
|---|---|
| Ingredient | Percent |
| Ground yellow corn | 55.5 |
| Soybean oil meal (44% protein) | 17.5 |
| Rolled oats | 10.0 |
| Sugar | 5.0 |
| Dried skim milk | 5.0 |
| Dried whey | 2.5 |
| Fish meal | 2.5 |
| Dicalcium phosphate | 1.5 |
| Iodized salt | 0.5 |
| Trace minerals[1] | + |
| Vitamins[2] | + |
| Total | 100.0 |

[1]Furnished the amounts of trace minerals in grams per ton: Fe, 18.2; Cu, 1.82; I, 1.09; Co, .18; and Zn, 30.
[2]Furnished the following amounts of vitamins per ton; Vitamin A, 4,000,000 I.U.; Vitamin D$_2$; 800,000 I.U.; riboflavin, 6 g.; pantothenic acid, 12 g.; niacin, 27 g.; choline chloride, 130 g.; Vitamin B$_{12}$, 20 mg.; folic acid, 120 mg.

TABLE XVI

Average Performance Data for Young Pigs Fed Several Levels of 2-(2-amino-5-thiadiazolyl)-1-methyl-5-nitroimidazaole In The Feed for 42 Days

|  | A | B | C | D | E |
|---|---|---|---|---|---|
|  | Control | Compound X (gm/ton) 50 | 100 | 200 | AUREO S.P. 250 |
| No. Pigs Started |  |  |  |  |  |
| Expt. 1 | 12 | 12 | 12 | 12 | 12 |
| Expt. 2 | 12 | 12 | 12 | 12 | 12 |
| Total | 24 | 24 | 24 | 24 | 24 |
| Mortality |  |  |  |  |  |
| Expt. 1 | 2 | 0 | 0 | 1 | 0 |
| Expt. 2 | 3 | 1 | 0 | 1 | 1 |
| Total | 5 | 1 | 0 | 2 | 1 |

TABLE XVI-continued

Average Performance Data for Young Pigs Fed Several Levels of 2-(2-amino-5-thiadiazolyl)-1-methyl-5-nitroimidazaole In The Feed for 42 Days

|  | A | B | C | D | E |
|---|---|---|---|---|---|
|  |  | Compound X (gm/ton) | | | AUREO S.P. |
|  | Control | 50 | 100 | 200 | 250 |
| Av. Initial Wt., lbs. | | | | | |
| Expt. 1 | 14.7 | 14.7 | 14.5 | 14.9 | 14.9 |
| Expt. 2 | 17.4 | 17.0 | 17.5 | 17.3 | 17.5 |
| Average | 16.0 | 15.8 | 16.0 | 16.1 | 16.2 |
| Av. Daily Gain, lbs. | | | | | |
| Expt. 1 | .56 | .63 | .65 | .71 | .69 |
| Expt. 2 | .51 | .60 | .83 | .76 | .63 |
| Average | .54 | .62 | .74 | .74 | .66 |
| Av. Feed/Gain Ratio | | | | | |
| Expt. 1 | 2.46 | 2.43 | 2.35 | 2.30 | 2.29 |
| Expt. 2 | 3.22 | 2.59 | 2.40 | 2.49 | 2.83 |
| Average | 2.84 | 2.51 | 2.38 | 2.40 | 2.56 |

EXAMPLE 56

| Ingredients | Amount mg. |
|---|---|
| 2-(2-amino-5-thiadiazolyl)-1-methyl-5-nitroimidazole | 480 |
| Magnesium stearate | 10 |
| Lactose | 600 |

After thoroughly mixing the above phase in 12 hard gelatin capsules. Each capsule will contain 40 mg. of active drug.

EXAMPLE 57

| Ingredients | Amount mg. |
|---|---|
| 2-(2-methylamino-5-thiadiazolyl)-methyl-5-nitroimidazole | 600 |
| Lactose | 1000 |

Mix thoroughly and place in 6 hard gelatin capsules. Each capsule contains 100 mg. of drug.

We claim:

1. A therapeutic composition useful for the control of bacterial infections in warm-blooded animals comprising an antibacterially effective amount of a nitroimidazole of the formula:

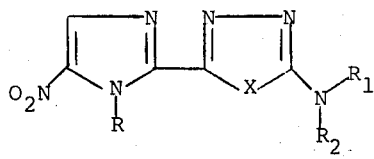

wherein R is selected from the group consisting of lower alkyl, hydroxy lower alkyl, lower alkanoyloxy lower alkyl and benzyl; X is sulfur; and $R_1$ and $R_2$ are selected from the group consisting of hydrogen, alkyl of 1 to 8 carbon atoms, hydroxy lower alkyl, lower alkoxy lower alkyl, cyclohexyl, formyl, lower alkanoyl, monochlorolower alkanoyl, dichloro lower alkanoyl and lower alkyl aminolower alkyl;

taken together is -N=CHN (lower alkyl)$_2$; or physiologically acceptable salts thereof; and an edible carrier.

2. The therapeutic composition according to claim 1, wherein the nitroimidazole is 2-(2-amino-5-thiadiazolyl)-1-methyl-5-nitroimidazole.

3. A method of controlling the growth of bacteria in warm-blooded animals which comprises administering to said animals an antibacterially effective amount of a nitroimidazole of the formula:

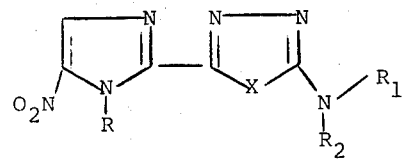

wherein R is selected from the group consisting of lower alkyl, hydroxy lower alkyl, lower alkanoyloxy lower alkyl and benzyl; X is sulfur; and $R_1$ and $R_2$ are selected from the group consisting of hydrogen, alkyl of 1 to 8 carbon atoms, hydroxy lower alkyl, lower alkoxy lower alkyl, cyclohexyl, formyl, lower alkanoyl, monochlorolower alkanoyl, dichloro lower alkanoyl and lower alkyl aminolower alkyl;

taken together is -N=CHN (lower alkyl)$_2$or physiologically acceptable salts thereof.

4. The method in accordance with claim 3 wherein the nitroimidazole is 2-(2-amino-5-thiadiazolyl)-1-(2-hydroxyethyl)-5-nitroimidazole.

5. The method in accordance with claim 3 wherein the nitroimidazole is 2-(2-amino-5-thiadiazolyl)-1-ethyl-5-nitroimidazole.

6. The method in accordance with claim 3 wherein the nitroimidazole is 2-(2-methylamino-5-thiadiazolyl)-1-methyl-5-nitroimidazole.

7. The method in accordance with claim 3 wherein the nitroimidazole is 2-(2-formamido-5-thiadiazolyl)-1-methyl-5-nitroimidazole.

8. The method in accordance with claim 3 wherein the nitroimidazole is 2-(2-amino-5-thiadiazolyl)-1-methyl-5-nitroimidazole.

9. The method in accordance with claim 3 wherein the nitroimidazole is 2-(2-dimethylamino-5-thiadiazolyl)-1-methyl-5-nitroimidazole.

* * * * *